Figure 1:
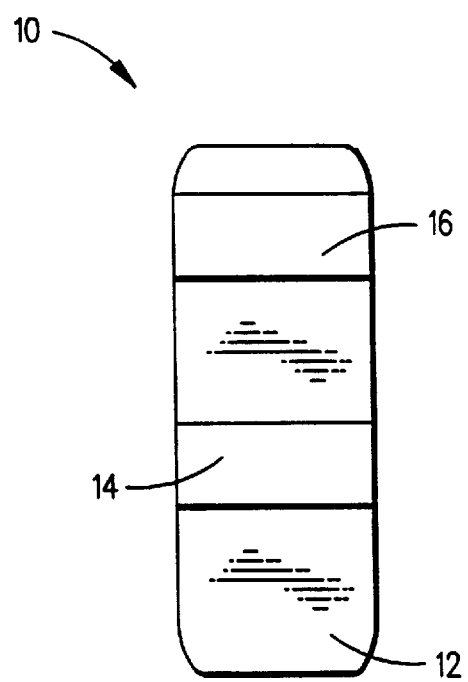

·

United States Patent [19]
Johnson

[11] Patent Number: 5,834,610
[45] Date of Patent: Nov. 10, 1998

[54] CONVERSION OF PYRIDINOLINE TO DEOXYPYRIDINOLINE

[76] Inventor: Gary M. Johnson, 1554 Kershner La., Elkhart, Ind. 46514

[21] Appl. No.: 852,131

[22] Filed: May 6, 1997

[51] Int. Cl.[6] ....................... C07D 213/65; C07D 213/74
[52] U.S. Cl. ............................................. 546/300; 546/347
[58] Field of Search ...................... 546/291, 300, 546/347

[56] References Cited

U.S. PATENT DOCUMENTS

| | | | |
|---|---|---|---|
| 5,300,434 | 4/1994 | Eyre | 435/240.2 |
| 5,350,855 | 9/1994 | Daniloff et al. | 546/291 |
| 5,455,179 | 10/1995 | Eyre | 436/536 |
| 5,502,197 | 3/1996 | Daniloff et al. | 546/281 |
| 5,527,715 | 6/1996 | Kung et al. | 436/547 |

*Primary Examiner*—Alan L. Rotman

[57] ABSTRACT

The present invention involves the synthetic conversion of pyridinoline (PYD) to deoxypyridinoline (DPD) via an intermediate ester which is subsequently cleaved. The transformation of PYD into a xanthate-type ester intermediate facilitates the subsequent removal of the substituted hydroxyl functionality thus providing the desired DPD. The method provides a new chemical pathway for the preparation of DPD, resulting in significantly increased yields as compared to traditional methods of product isolation.

10 Claims, 1 Drawing Sheet

CONVERSION OF PYRIDINOLINE TO DEOXYPYRIDINOLINE

BACKGROUND OF THE INVENTION

Collagen is present in various forms in all tissue. It is now well accepted that collagen has the form of amino acid chains cross-linked by pyridinium cross-links. The pyridinium crosslinks are formed from three hydroxylysine residues, two of which are from the terminal (non-helical) peptides of the collagen molecule that are enzymatically converted to aldehydes before reaction and a third hydroxylysine situated in the helical portion of a neighboring collagen molecule. Two pyridinium crosslinks, pyridinoline (PYD) and deoxypyridinoline (DPD), have been identified. There have been described in the literature techniques for the measurement of pyridinoline in urine by use of enzyme labeled anti-PYD to form a pyridinoline-enzyme labeled complex which can be detected by an enzyme-linked immunosorbant assay. While the analysis for PYD is useful as a means of screening for osteoporosis and rheumatoid arthritis, its presence in connective tissue, as well as in bone, can cause skewed results for the diagnosis of osteoporosis or bone degradation. Accordingly, immunoassays for dexoypyridinoline (DPD), which is only found in bone, have become preferred over those for PYD for the early detection of bone degradation.

Testing for DPD can be carried out by contacting a fluid test sample, e.g. urine, with a labeled antibody specific for DPD. A particularly convenient method for DPD analysis involves the use of a test strip of the type depicted in FIG. 1. Referring to FIG. 1, strip 10 having a labeled anti-DPD antibody complex (typically with gold sol as the labeling material to provide a gold sol-DPD antibody complex) binds with DPD in the fluid test sample applied to the application zone 12 of the strip 10 and migrates through the first capture zone 14 and second capture zone 16. In the first capture zone 14 there is immobilized DPD which captures unbound, labeled anti-DPD. The labeled antibody, which was not captured in the first capture zone because it combined with DPD in the fluid test sample, is captured in the second capture zone 16 by anti-DPD antibodies which are immobilized in this zone. The DPD concentration in the test sample can be determined by spectrophotometrically measuring the amount of labeled DPD captured in the first capture zone 14, or more accurately by use of an algorithmic treatment of reflectance measurements from both zones 14 and 16.

The first capture zone 14 requires immobilized DPD with which the labeled anti-DPD, which hasn't reacted with DPD in the fluid sample, can combine to become immobilized in this capture zone. This sort of disposable test system requires the use of considerable amounts of DPD which, when obtained from animal bone, is quite expensive. The expense involved with the procurement of natural DPD has led to attempts to synthesize this material and thereby reduce the cost of diagnostic test strips which employ DPD in DPD detection systems.

One method for the synthesis of DPD as well as PYD and derivatives thereof is disclosed in published European Patent Application 0 556 152 A$_1$. In this procedure a compound of the formula:

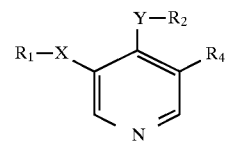

is reacted with an R group which is defined as X$_5$—CH$_2$—CHX$_1$—Z—R$_3$ wherein the R, X, Y and Z groups are selected to provide DPD, PYD or various derivatives thereof.

An alternative to preparation of DPD by an entirely synthetic means involves the conversion of PYD which is relatively plentiful in view of the fact that it is the major pyridinium compound obtained from the bone as contrasted to DPD which is obtained only in very small quantities. The isolation of DPD and PYD from various sources such as bone gel, sheep bones and chicken bones is described by Acil et. al., *Scan. J. Clin & Lab. Invst.*, 56 (3), 275–83, (1996). The first isolation and identification of DPD and PYD is discussed by Fujimoto et. al. in *Biochem & BioPhys. Res. Comm.*, 84 (1), 52–57 (1978). The degradation affects of U.V. light on DPD and PYD and HPLC methodology for their measurement are described by Blumshon et. al., *Clin. Chem*, 41 (8), 1195–7 (1995) and Takahashi et. al, *Anal. Biochem.*, 232, 158–62 (1995) respectively.

SUMMARY OF THE INVENTION

The present invention involves the chemical conversion of pyridinoline to deoxypyridinoline. The method comprises the steps of:

a) reacting pyridinoline with an alkali metal hydride with heating in an appropriate solvent using an equivalents ratio of hydride to pyridinoline of from about 1 to about 5 to obtain deprotonated pyridinoline;

b) reacting the deprotonated pyridinoline from, step (a) with an excess of carbon disulfide to obtain an intermediate dithiocarbonate;

c) reacting the intermediate dithiocarbonate with an alkyl iodide to obtain the corresponding S-alkyl dithiocarbonate;

d) after cooling the reaction, adding thereto an aqueous acid to quench the S-alkyl thiocarbonate; and e) reacting the S-alkyl dithiocarbonate with an alkyl tin hydride to obtain deoxypyridinoline.

DESCRIPTION OF THE INVENTION

The method of the present invention for converting PYD to DPD is depicted in Scheme I where PYD.(HFBA)$_n$ is reacted with an alkali metal hydride in order to deprotonate the PYD. (HFBA)$_n$ is heptafluorobutyric acid of some value n where n is from 1 to 4. The isolation is done in the presence of HFBA, so that the DPD is present in its isolated form as the acid salt. Suitable alkali metal hydrides include NaH, KH, LiH and CsH. While the goal is to deprotenate the hydroxyl group on the alkyl sidechain, so that it can be esterified, it is likely that the carboxylic groups are also deprotenated and then reprotonated later in the procedure. The reaction is carried out in a suitable solvent, i.e. THF, toluene, xylene, light petroleum or hexane at an elevated temperature, depending on the boiling point of the solvent, for a period of time sufficient to deprotonate the hydroxyl group of the PYD. While tetrahydrofuran is depicted as the solvent in Scheme I, other suitable solvents such as those mentioned above may be used. The equivalents ratio of alkali metal hydride to PYD should be from about 1 to about 5 in order to achieve deprotonation without precipitating the deprotonated species from the reaction solution. A preferred ratio is in the range of from 3 to 4. A catalyst such as imidazole is normally added to the reaction in a catalytic amount to speed up the rate of reaction. The reaction is carried out under an inert atmosphere, e.g. argon and in the dark due to light sensitivity and instability of the compounds.

After deprotonation, the PYD is reacted with carbon disulfide to provide the intermediate dithiocarbonate. This step can be carried out without isolation of the deprotonated PYD. This step involves heating the reaction up to the boiling point of the solvent and is likewise carried out in the dark under an inert atmosphere. The amount of carbon disulfide used is typically up to a 50 fold molar excess. The resultant of this step of the reaction is an intermediate dithiocarbonate which is reacted with an alkyl iodide of the formula ZI where Z is an alkyl group of 1 to 10 carbon atoms (preferably 1 to 6) to obtain the corresponding alkyl dithiocarbonate (designated ester in Scheme I).

After formation of the ester, the reaction is cooled and then quenched with an aqueous acid such as aqueous acetic acid, HCl or HBr. The reprotonated S-alkyl dithiocarbonate is then reacted with an excess of alkyl tin hydride, $Sn(Q)_3H$ where Q is an alkyl group of 1 to 10 carbon atoms (preferably 3 to 6), to cleave the intermediate thiocarbonate ester thereby providing the desired DPD.

Recovery of DPD is accomplished by HPLC following published literature procedures.

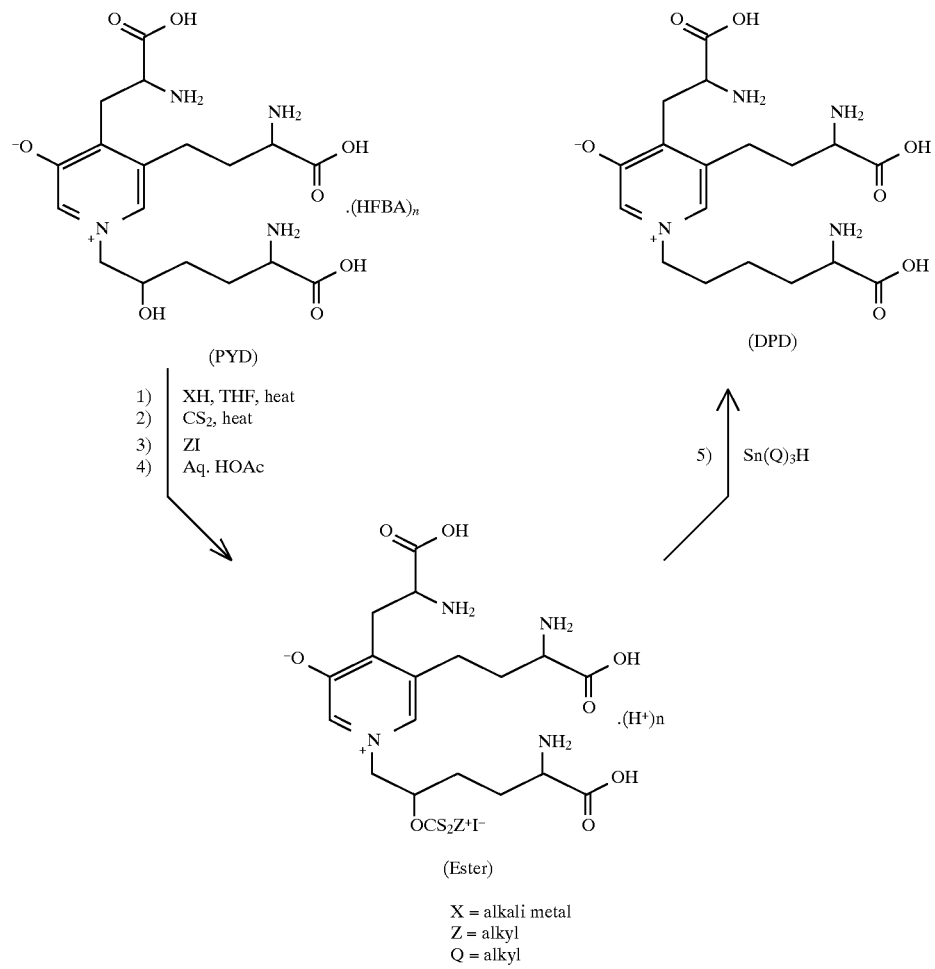

Scheme I

X = alkali metal
Z = alkyl
Q = alkyl

EXAMPLE

To PYD (1×total wt., ≈100 μmol) naturally isolated from bone gelatin in anhydrous tetrahydrofuran (3 mL), under argon in the dark at room temperature, was added a catalytic amount of imidazole (<0.05 molar equivalents) in one portion followed by sodium hydride (NaH, 60%, 3 molar equivalents) in one portion. The reaction was warmed in an oil bath (≈50° C.) for about 2 hours under argon in the dark. Carbon disulfide (CS, 50 molar equivalents) was then added via syringe with the heating being maintained for an additional half hour. Methyl iodide (MeI, 50 molar equivalents) was then added via syringe and the heating was further maintained for half an hour. The solution was then cooled (≈0.5 h) whereupon aqueous acetic acid (50%, 0.5 mL) was added to quench the reaction followed by concentration in vacuo to dryness. Toluene (4 mL) was added and the mixture was concentrated in vacuo (repeated 2X) to azeotrope residual moisture.

Toluene (3 mL) was added in one portion to the crude reaction solids under argon in the dark at room temperature, followed by tri-n-butyltin hydride (Bu$_3$SnH, 50 molar equivalents) in one portion via syringe. The reaction was then warmed in an oil bath ($\approx$70°–80° C.) for about 20 hours under argon in the dark and then concentrated in vacuo to remove toluene. Residual Bu$_3$SnH was decanted from solid crude product after which the product was placed under high vacuum for about 0.5 hours.

Examination by analytical HPLC against known PYD and DPD standards demonstrated conversion of PYD to DPD. Conversion was about 3:1 (PYD:DPD) with very little decomposition or side products being formed in the reaction process. Incomplete conversion may be due to steric effects, residual moisture, or non-optimized reaction conditions. Immunological activity, which was ten times greater than that of the starting material, was characteristic of DPD relative to PYD.

It was necessary to purify the crude product as quickly as possible after work up since, if left crude, the DPD/PYD underwent degradation and/or further reaction with residual tin residues. Accordingly, the DPD and recovered PYD were purified and desalted by preparative HPLC. Analytical HPLC and UV analysis as well as the immunological activity of synthetic DPD was consistent with naturally isolated material. The separated PYD can be recycled through the reaction process to provide additional DPD.

What is claimed is:

1. A method for the chemical conversion of pyridinoline to deoxypyridinoline which comprises the steps of:
   a) reacting pyridinoline with an alkali metal hydride in an appropriate solvent with heating wherein the equivalents ratio of hydride to pyridinoline is from about 1 to 5 to obtain deprotonated pyridinoline;
   b) reacting the deprotonated pyridinoline with an excess of carbon disulfide to obtain an intermediate dithiocarbonate;
   c) reacting the intermediate dithiocarbonate with an alkyl iodide to obtain the corresponding S-alkyl dithiocarbonate;
   d) cooling the reaction followed by adding an aqueous acid to the reaction to quench the S-alkyl dithiocarbonate; and
   e) reacting the S-alkyl dithiocarbonate with an alkyl tin hydride to obtain deoxypyridinoline.

2. The method of claim 1 wherein the ratio of hydride to pyridinoline is from 3 to 4.

3. The method of claim 1 wherein the carbon disulfide is present in up to a 50 molar excess of the deprotonated pyridinoline.

4. The method of claim 1 wherein the pyridinoline is reacted with the alkali metal hydride in the presence of (HFBA)$_n$ where n is from 1 to 4.

5. The method of claim 1 wherein the alkyl iodide contains from 1 to 10 carbon atoms in the alkyl group.

6. The method of claim 5 wherein the alkyl iodide contains from 1 to 6 carbon atoms.

7. The method of claim 1 wherein the alkyl tin hydride contains from 1 to 10 carbon atoms in the alkyl group.

8. The method of claim 7 wherein the alkyl tin hydride contains from 3 to 6 carbon atoms.

9. The method of claim 1 wherein the reaction is carried out in a solvent selected from the group consisting of tetrahydrofuran, toluene, xylene or hexane.

10. A method for the chemical conversion of pyridinoline to deoxypyridinoline which comprises the steps of:
    a) reacting bone gelatin pyridinoline with an alkali metal hydride in tetrahydrofuran with heating wherein the equivalents ratio of hydride is from 3 to 4 to deprotonate the pyridinoline;
    b) reacting the deprotonated pyridinoline with up to a 50 molar excess of carbon disulfide to obtain an intermediate dithiocarbonate;
    c) reacting the intermediate dithiocarbonate with an alkyl iodide having from 1 to 6 carbon atoms to obtain the corresponding S-alkyl dithiocarbonate;
    d) cooling the reaction and adding aqueous acetic acid to quench the S-alkyl dithiocarbonate;
    e) reacting the S-alkyl dithiocarbonate with an alkyl tin hydride having 3 to 6 carbon atoms to obtain deoxypyridinoline; and
    f) recovering the deoxypyridinoline.

* * * * *